United States Patent [19]

Friese

[11] Patent Number: 4,610,659
[45] Date of Patent: Sep. 9, 1986

[54] TAMPON PACK

[75] Inventor: Axel Friese, Wuppertal, Fed. Rep. of Germany

[73] Assignee: Johnson & Johnson G.m.b.H., Dusseldorf, Fed. Rep. of Germany

[21] Appl. No.: 662,423
[22] PCT Filed: Jan. 26, 1984
[86] PCT No.: PCT/DE84/00021
  § 371 Date: Sep. 21, 1984
  § 102(e) Date: Sep. 21, 1984
[87] PCT Pub. No.: WO84/02840
  PCT Pub. Date: Aug. 2, 1984

[30] Foreign Application Priority Data

Jan. 28, 1983 [DE] Fed. Rep. of Germany ....... 3302932

[51] Int. Cl.$^4$ .............................................. A61F 13/20
[52] U.S. Cl. ......................................... 604/11; 604/15
[58] Field of Search ....................... 604/15, 13, 12, 11, 604/358

[56] References Cited

U.S. PATENT DOCUMENTS

3,139,886 7/1964 Tallman et al. ..................... 604/12
3,499,447 3/1970 Mattes et al. ...................... 604/12
3,674,025 7/1972 Bleuer ............................... 604/12

Primary Examiner—John D. Yasko
Attorney, Agent, or Firm—Jason Lipow

[57] ABSTRACT

A tampon pack, in particular for female hygiene, as indicated, which consists of a tampon applicator (1) having an applicator shell (2) and a plunger (3) telescopically mounted therein to be axially movable, and of a tampon (4) which is located in the applicator shell (2), has a withdrawal cord (5) and can be pushed out of the applicator shell (2) by means of the plunger (3), a flexible packaging film (6) being provided in the region of the introduction end (7) of the tampon (4) and being held on the applicator shell (2). The special point of the tampon pack is that the packaging film (6) surrounds substantially the entire surface of the tampon (4), is made to be substantially impermeable to water vapor and is provided, on the inside facing the tampon (4), with a coating having a high coefficient of sliding friction. An increase in the volume of the tampon, caused by moisture absorption during the storage period, is thereby prevented and/or alleviated on all sides, and it is ensured that the tampon (4) can easily be pushed out of the applicator shell (2). Moreover, packaging material is saved by this type of wrapping the tampon (4). (FIG. 1).

7 Claims, 9 Drawing Figures

TAMPON PACK

The invention relates to a tampon pack, in particular for female hygiene, consisting of a tampon applicator having an applicator shell and a plunger telescopically mounted therein to be axially movable, and of a tampon which is located in the applicator shell, has a withdrawal cord and can be pushed out of the applicator shell by means of the plunger, a flexible packing film being provided in the region of the introduction end of the tampon and being held on the applicator shell.

Tampon packs of this type are known. For example in British Patent Specification No. 1,262,887, a tampon applicator is described which essentially consists of an applicator shell and a plunger which is axially movable therein. At its introduction end, the applicator is closed by a cap of a plastic film. On the introduction end of the applicator, a sleeve of the plastic film is arranged, which sleeve projects beyond the introduction end of the applicator. The open end of the sleeve is closed by folding, forming the said cap. When the applicator is used, the tampon is forced by axial pressure on the plunger from the inside against the folded closed end of the cap, which thus opens and clears the path for pushing the tampon out.

Tampons of this type increase their volume by absorbing moisture or fluid. When this happens while the tampon is still inside the applicator, for example when stored in a humid environment, the tampon can jam in the applicator shell due to the increased volume and make it considerably more difficult to push it out of the applicator. For this reason, a substantial increase in volume of the tampon must be prevented by suitable means, and this is possible, for example, by excluding water vapor.

Admittedly, the cap of the known tampon applicator will be able, if it consists of a suitable material, to prevent the penetration of water vapor through the introduction end of the applicator into the tampon. However, the rear tampon end can still absorb water vapor through the hollow plunger and/or through the gap between the plunger and applicator shell. For this reason, further measures are necessary in order to avoid an increase in volume of the tampon in the known applicator by the absorption of water vapor.

The invention is based on the object of developing a tampon pack of the type set forth above, in such a way that the tampon pack fulfills its purpose even after a prolonged storage period, in particular in a relatively humid environment, that is to say to prevent an increase in the volume of the tampon, which is caused by the absorption of water vapor and would make it more difficult to push the tampon out of the applicator. At the same time, the quantity, which is required per tampon pack and is significant for this mass-produced article, of valuable packaging material impermeable to water vapor is to be reduced.

According to the invention, this object is achieved when the packaging film surrounds substantially the entire surface of the tampon, is made to be substantially impermeable to water vapor and is provided, on the inside facing the tampon, with a coating having a low coefficient of sliding friction.

In the normal case, this prevents the tampon from absorbing relatively large quantities of water vapor, while it is in storage, and thus substantially increasing its volume. If nevertheless, in exceptional cases, the packaged tampon tries to expand for any reason, its increase in volume is limited virtually on all sides by the packaging film which is in taut contact with the tampon surface. Moreover, the coating, having a low coefficient of sliding friction, on the inside of the packaging film ensures in these cases that the tampon can still be relatively easily pressed out of this film and out of the applicator shell.

Wrapping of only the tampons with a packaging film impermeable to water vapor allows the packaged tampons to be held in intermediate storage for a longer period, before they are made up with the applicators. During the intermediate storage, the tampons substantially retain the volume given to them during manufacture and can therefore be introduced into the applicators at a later time, if desired.

Due to the fact that only the actual tampon and no longer the entire arrangement consisting of applicator and tampon is surrounded by a relatively high-value packaging film, a large quantity of this material is saved. A simpler, for example mechanically less strong and therefore less expensive packaging material is then adequate for wrapping the complete arrangement of applicator and tampon. It is then also possible to combine a plurality of tampon packs in one common packaging, whereby further packaging material is saved, without having to abandon packaging of each individual tampon.

Various preferred embodiments of the tampon pack according to the invention are indicated in patent claims 2 to 11.

As claimed in claim 12, it is advantageous when the front end of the plunger is cylindrical and has an external diameter which is smaller than that of the tampon. As a result, an annular space is provided in front of the front end of the plunger and the applicator shell, which space facilitates the turning-over of the packaging film at the rear end of the tampon, when the tampon is pushed out of the applicator shell. The smaller external diameter of the front plunger end also leads to a saving of plunger material.

Finally, it is advantageous when the edge of the rear opening of the applicator shell is flanged inwards and the plunger has an annular bead on the longitudinal portion located in the applicator shell. The rear end of the applicator shell thus serves as a rear stop for the annular bead of the plunger, so that inadvertent sliding of the plunger out of the applicator shell is prevented.

The invention is explained below by reference to illustrative embodiments represented diagrammatically in the drawing in which.

According to FIGS. 1 to 8, the tampon pack essentially consists of a tampon applicator 1 which comprises an applicator shell 2 and a plunger 3 telescopically mounted therein to be axially movable, and a tampon 4 which is located in the applicator shell 2 and has a front tampon portion 4a and a rear tampon portion 4b and a withdrawal cord 5.

Figure 1:
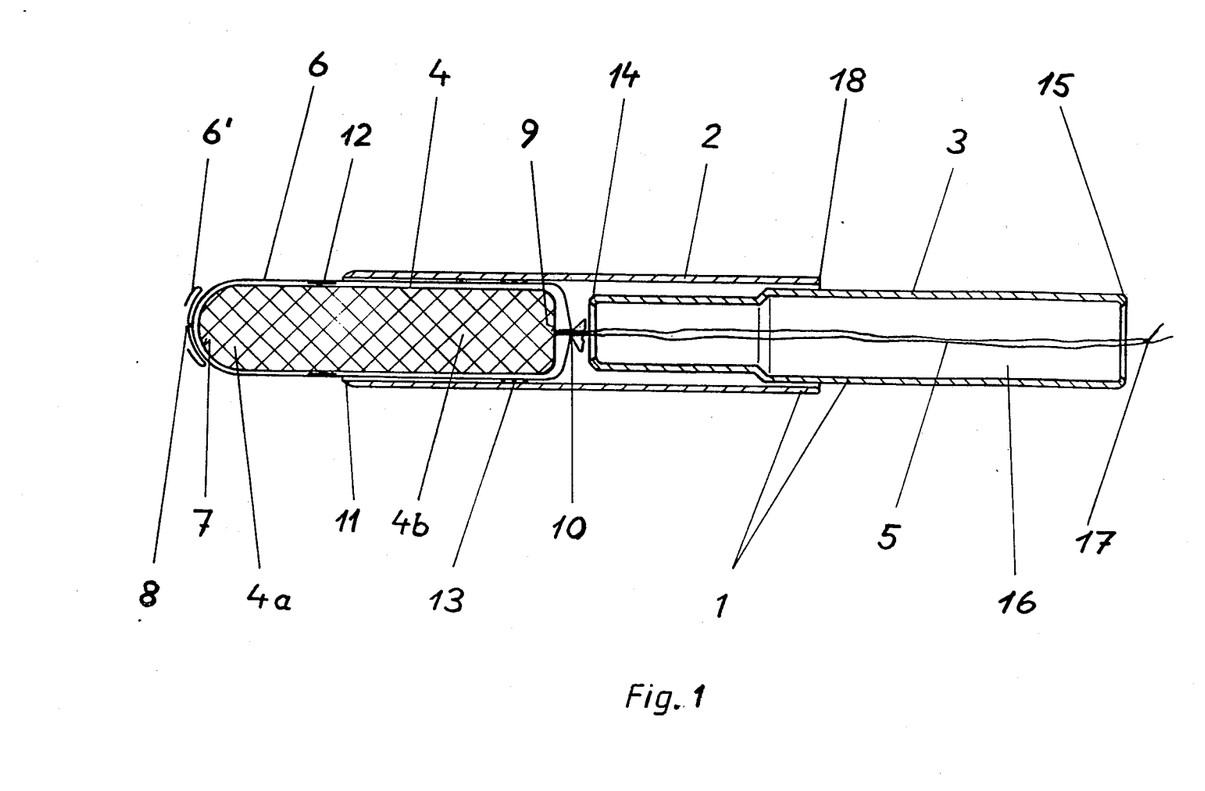
FIGS. 1 to 8 show axial longitudinal sections through various embodiments of the tampon pack and FIG. 9 shows a cross-section through the tampon pack according to FIG. 8, along the section line A—A.

According to FIG. 1, a packaging film 6, for example of cellulose hydrate or regenerated cellulose, which is impermeable to water vapor surrounds substantially the entire surface of the tampon 4. On the side facing the tampon 4, the packaging film 6 is provided with a coating which is not shown in the drawing and has a low coefficient of sliding friction. This coating consists, for example, of a coat of polymer. At the introduction end 7 of the tampon 4, the packaging film 6 has a conventional front closure 8 which has preferably been made by a gathered seal. For clarity, the front end 6' of the packaging film 6 is not shown in the drawing as being in close contact with the closure 8.

At the rear end 9 of the tampon 4, a rear closure 10 of the packaging film 6 is provided.

The front tampon portion 4a of the tampon 4 protrudes beyond the introduction end 11 of the applicator shell 2 and, on this portion 4a, the packaging film 6 is provided with a tear-off strip 12 in the peripheral direction of the tampon 4. The packaging film 6 can thus be severed in a simple manner from the introduction end 7 of the tampon 4 before the latter is used.

In that portion which cylindrically surrounds the portion 4b, located within the applicator shell 2, of the tampon 4, the packaging film 6 is fastened by means of junctions 13 to the inside of the applicator shell 2 and is thus axially fixed.

The junctions 13 can be formed, for example, by using an adhesive or by means of heat-sealing. The area of such a junction 13 can, for example, have substantially the shape of a point or a strip, or it can be annular, following the internal periphery of the applicator shell 2. If the applicator shell 2 and the packaging film 6 are in contact, these two can also be mutually joined over the whole area, the junction 13 then representing a cylindrical surface.

The front end 14 of the plunger 3 is located in the applicator shell 2 which, over its entire length, has a substantially constant external diameter and a substantially constant internal diameter. This end 14 is of cylindrical shape and its external diameter is smaller than that of the tampon 4. This facilitates the turning-over of the packaging film 6 remaining in the applicator shell 2, when the tampon 4 is pushed out of the applicator shell 2.

As compared with the front end 14 of the plunger 3, the remaining plunger portion extending up to the rear end 15 of the plunger 3 has a larger external diameter which, for guiding the plunger 3 in the applicator shell 2, is only slightly smaller than the internal diameter of the applicator shell 2.

The withdrawal cord 5 extends from the rear end 9 of the tampon 4 through the rear closure 10 of the packaging film 6 and through a cavity 16 in the plunger 3 up to the rear end 15 of the latter, where the end 17 of the withdrawal cord 5 can be gripped.

For using the tampon pack, the tear-off strip 12 is first detached and the packaging film 6 is removed from the introduction end 7 of the tampon 4. The tampon applicator 1 with the tampon 4 is then introduced into the body cavity. By firmly holding the applicator shell 2 and simultaneously exerting an axial pressure in the direction of introduction on the plunger 3, the tampon 4 is pushed out of the applicator shell 2 and the remaining part of the packaging film 6. While the tampon 4 is sliding out of the applicator shell 2, the packaging film 6 at the rear end 9 of the tampon 4 is turned over. After the tampon 4 has been pushed out of the applicator shell 2 and correctly positioned in the body cavity, the tampon applicator 1 with the packaging film 6 held thereon is retracted out of the body cavity.

Figure 2:
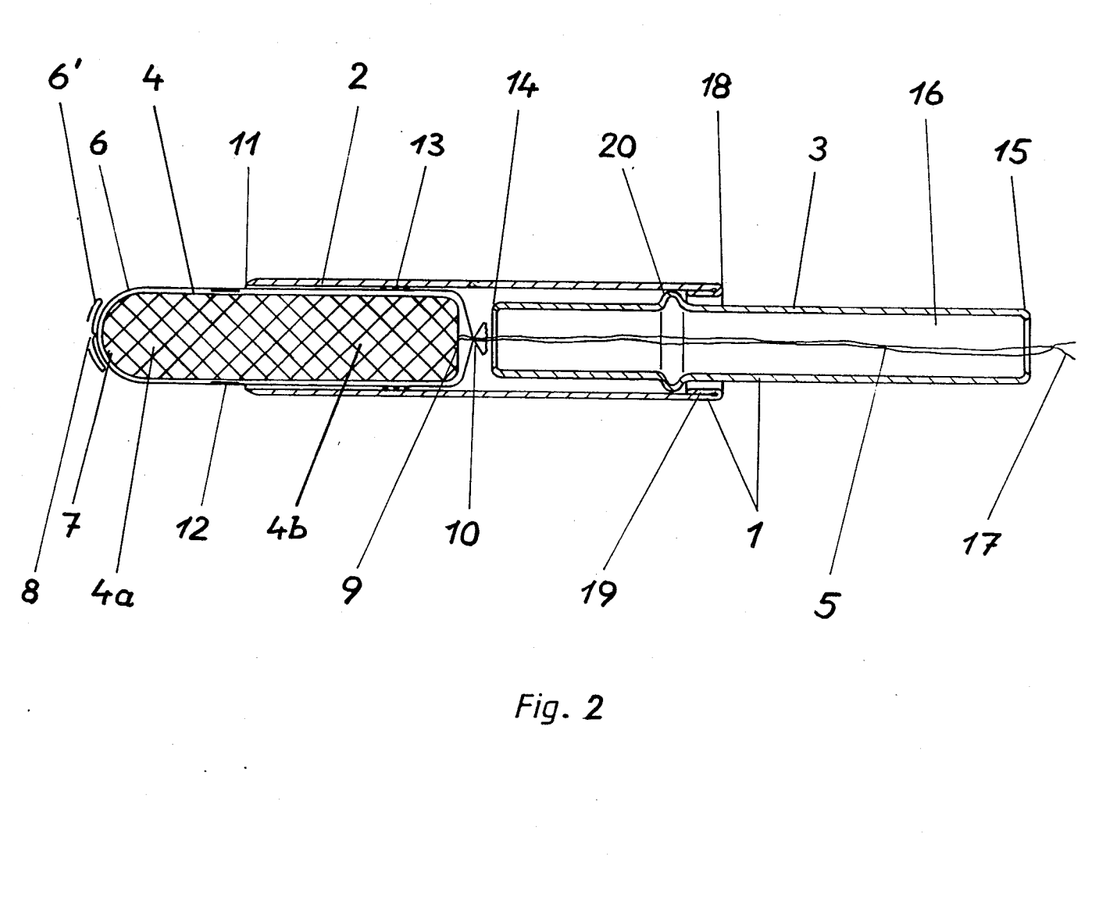

FIG. 2 differs from FIG. 1 in that the external diameter of the plunger 3 is substantially the same over the entire length thereof and corresponds to the smaller external diameter at the front end 14 of the plunger 3 according to FIG. 1. In the embodiment according to FIG. 2, however, the edge 19 of the applicator shell 2 is flanged inwards at the rear opening 18 thereof, and the plunger 3 has an annular bead 20 on the longitudinal portion located in the applicator shell 2. The flanged edge 19 of the applicator shell 2 represents a stop for the annular bead 20 of the plunger 3, whereby inadvertent sliding of the plunger 3 out of the applicator shell 2 is avoided.

Figure 3:
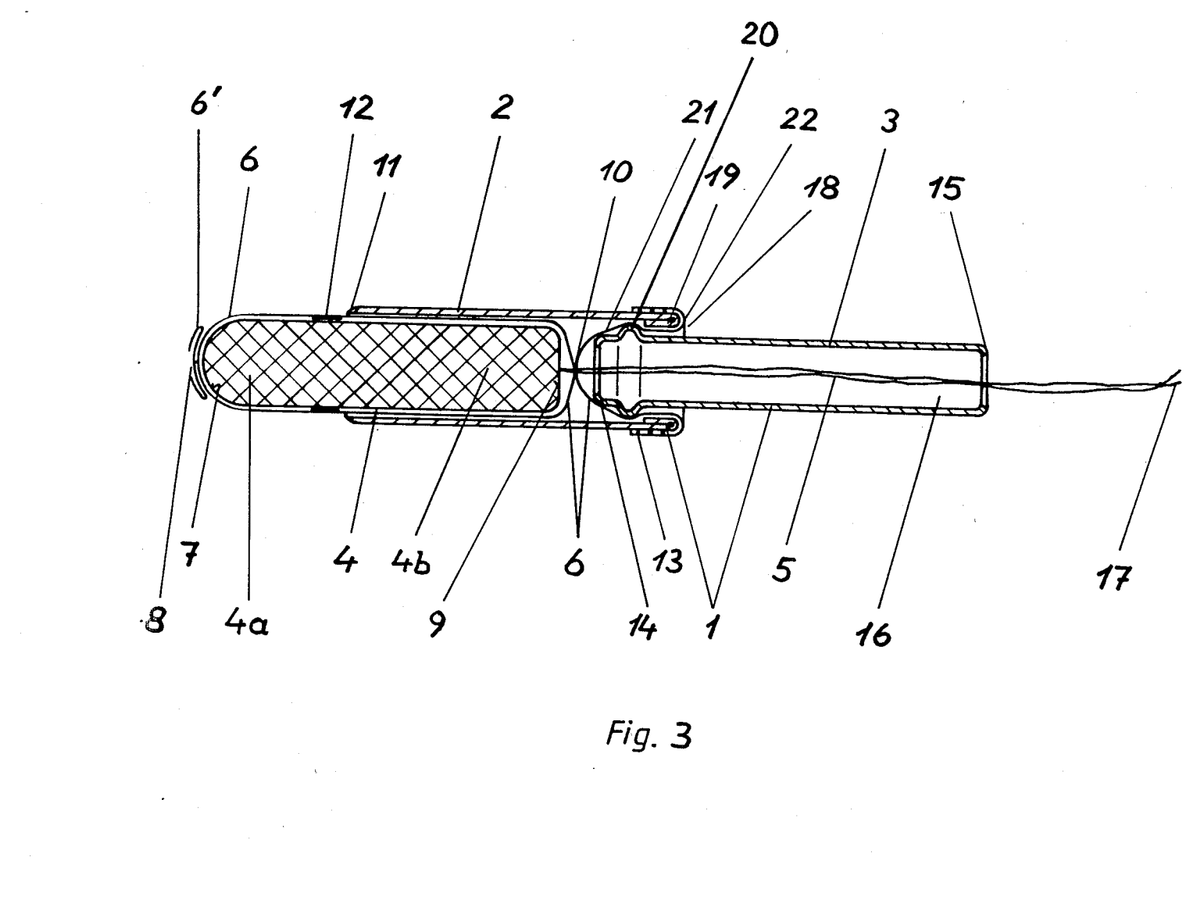

According to FIG. 3, the packaging film 6 is in fact closed at the rear end 9 of the tampon 4, as in the embodiments according to FIGS. 1 and 2, but the packaging film 6 extends from its rear closure 10 in the form of a bag-like prolongation 21 through the rear opening 18 of the applicator shell 2. The edge zone 22 of the prolongation 21 is folded over outwards around the rear edge 19 of the applicator shell 2 and is fixed there at the junctions 13, for example by gluing or sealing to the applicator shell 2. That portion of the plunger 3 which is located in the interior of the applicator shell 2 is surrounded by the bag-like prolongation 21 of the packaging film 6. Moreover, as compared with FIG. 2, this portion of the plunger 3 is made substantially shorter, so that material for the plunger 3 and the applicator shell 2 is saved. This shortening is also possible in the other embodiments of the tampon packs, shown in the drawing.

When using the tampon pack according to FIG. 3, the plunger 3 is pressed in the direction of the tampon 4, after the packaging film 6 has been removed from the introduction end 7 of the tampon 4. The rear closure 10 of the packaging film 6 is thus opened, and the front end 14 of the plunger 3 strikes the rear end 9 of the tampon 4 which is then pushed out of the applicator shell 2 in the usual way.

Figure 4:
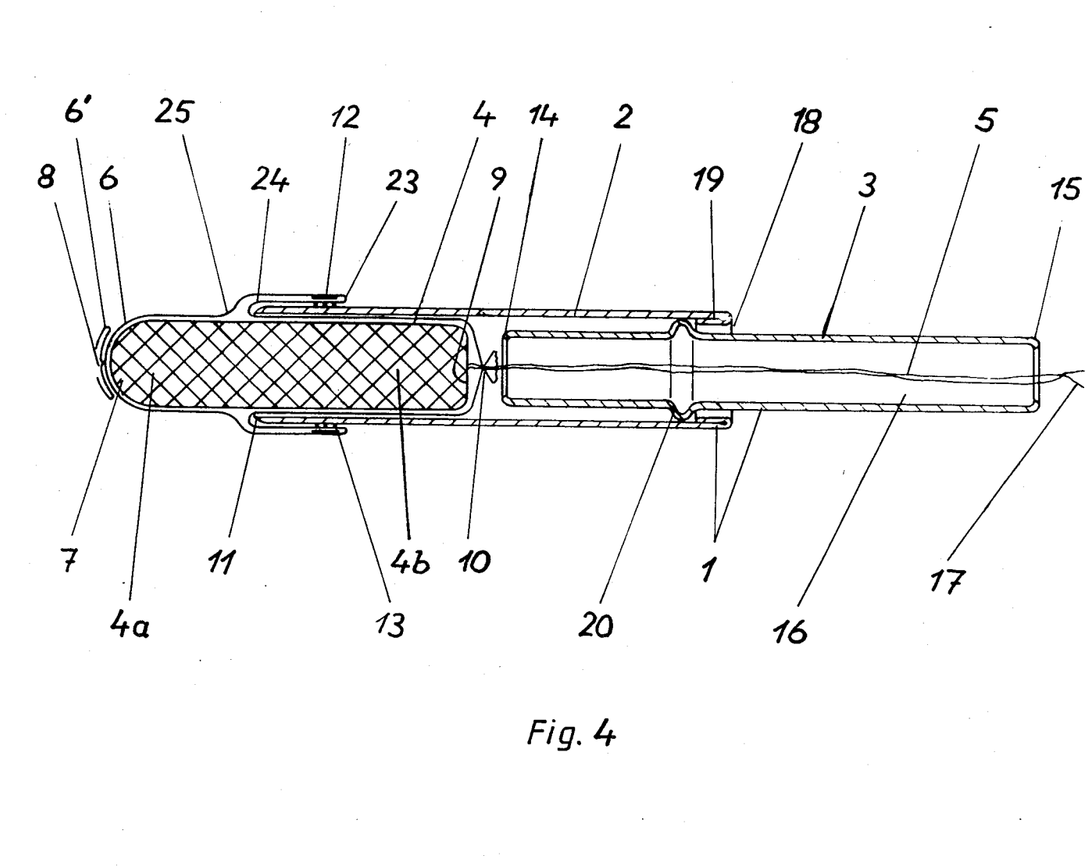

According to FIG. 4, the packaging film 6 is fixed to the applicator shell 2 in the region of the introduction end 11 thereof. The packaging film 6 has, where it surrounds the cylindrical portion of the tampon 4, a double-walled peripheral strap 23 with an inner strap wall 24 and an outer strap wall 25. The peripheral strap 23 surrounds the introduction end 11 of the applicator shell 2 like a bag. The inner strap wall 24 is fixed at junctions 13 on the outside of the applicator shell 2 and merges into that portion of the packaging film 6 which extends into the interior of the applicator shell 2 and towards the rear end 9 of the tampon 4. The outer strap wall 25 of the packaging film 6 merges into the front portion thereof, which envelopes the introduction end 7 of the tampon 4. The tear-off strip 12 of the packaging film 6 is located on the outer strap wall 25.

Figure 5:
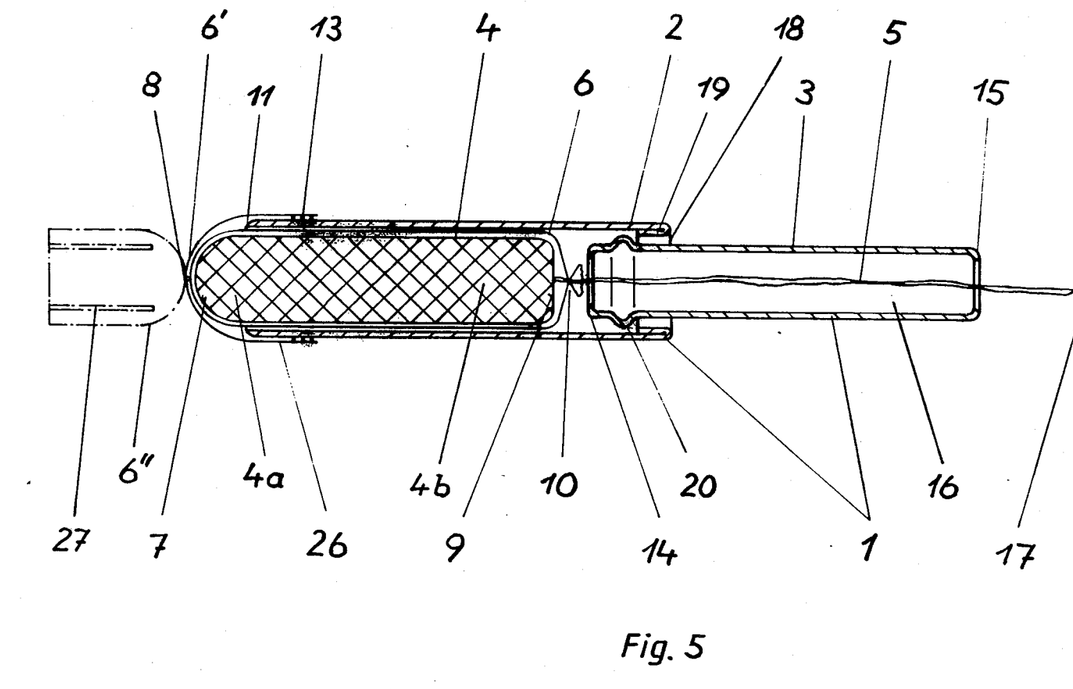

According to FIG. 5, the front end 6' of the packaging film 6 at the introduction end 7 of the tampon 4 is given such a length that this end 6' can be turned over and laid over the introduction end 11 of the applicator shell 2, forming a closure cap 26, and fixed thereto by means of junctions 13. The packaging film 6 and the closure cap 26 thus consist of the same material.

To clarify the production of this embodiment, the front end 6' of the packaging film 6, in the form of a cylinder 6" with rounded bottom, is additionally shown in front of the closure cap 26 by broken lines in FIG. 5. This form of the cylinder 6" takes up the end 6' of the packaging film 6, before it is turned over the introduction end 11 of the applicator shell 2, with formation of the closure cap 26. To facilitate the turning-over, the cylinder 6" has slots 27 which are parallel to the axis and two of which are shown in FIG. 5.

For pushing the tampon 4 out of the applicator shell 2, the front closure 8 of the packaging film 6 is opened by the axial pressure of the tampon 4. For this reason, the tear-off strip 12 is superfluous in this embodiment of the tampon pack.

Figure 6:
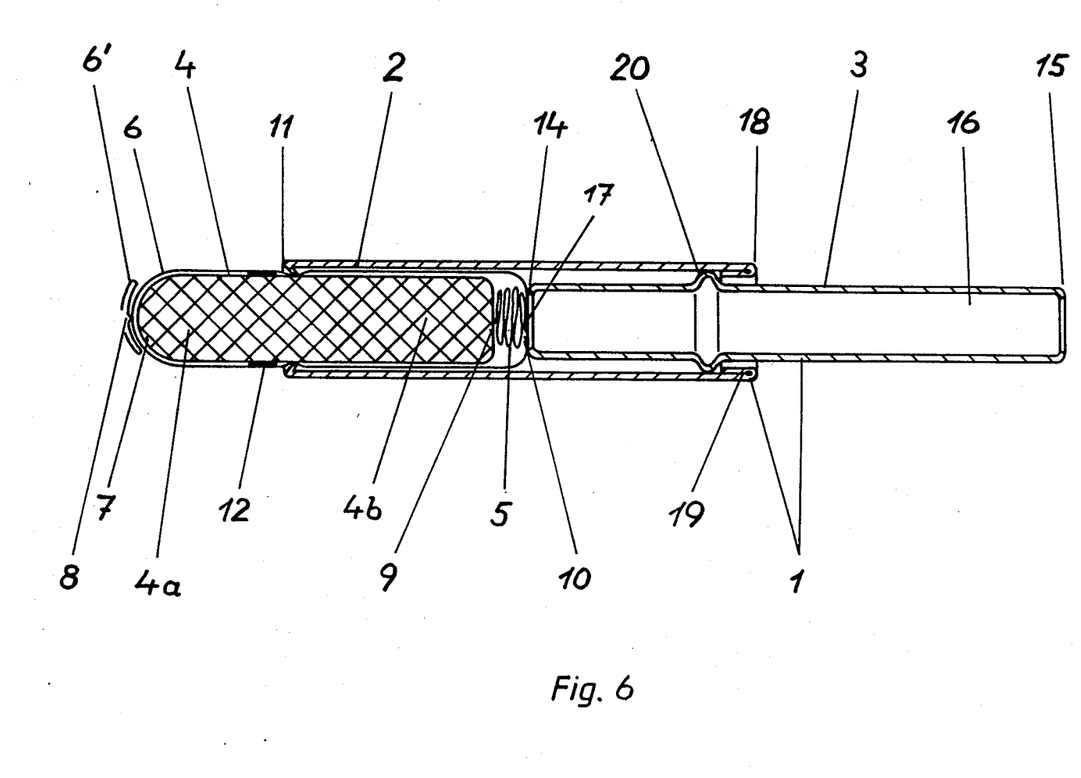

According to FIG. 6, the packaging film 6 is only clamped in radially between the tampon 4 and the inside, of reduced diameter, of the introduction end 11 of the applicator shell 2. The introduction end 11 is drawn slightly inwards and is supported on the periphery of the packaging film 6 and the tampon 4 located underneath. When the tampon 4 is pushed out of the applicator shell 2, the packaging film 6 builds up in the applicator shell 2.

FIG. 6 also shows that the withdrawal cord 5 is applied to the rear end 9 of the tampon 4 and, together with the tampon 4, is surrounded by the packaging film 6. To ensure that, in this case, the withdrawal cord 5 is extended, after the tampon 4 has been introduced into the body cavity, and protrudes from the body cavity, the rear end 17 of the withdrawal cord 5 is fixed to the rear closure 10 of the packaging film 6. When, after the tampon has been introduced into a body cavity, the tampon applicator 1 and hence the packaging film 6, clamped in between the introduction end 11 of the applicator shell 2 and the plunger 3, is retracted, the withdrawal cord 5 is extended in the direction of pull, so that its rear end 17 in the end is located outside the body cavity. It is also possible, however, in the embodiment of the tampon pack according to FIG. 6, for the withdrawal cord 5 to be arranged in an extended form, as shown for the other embodiments.

Figure 7:
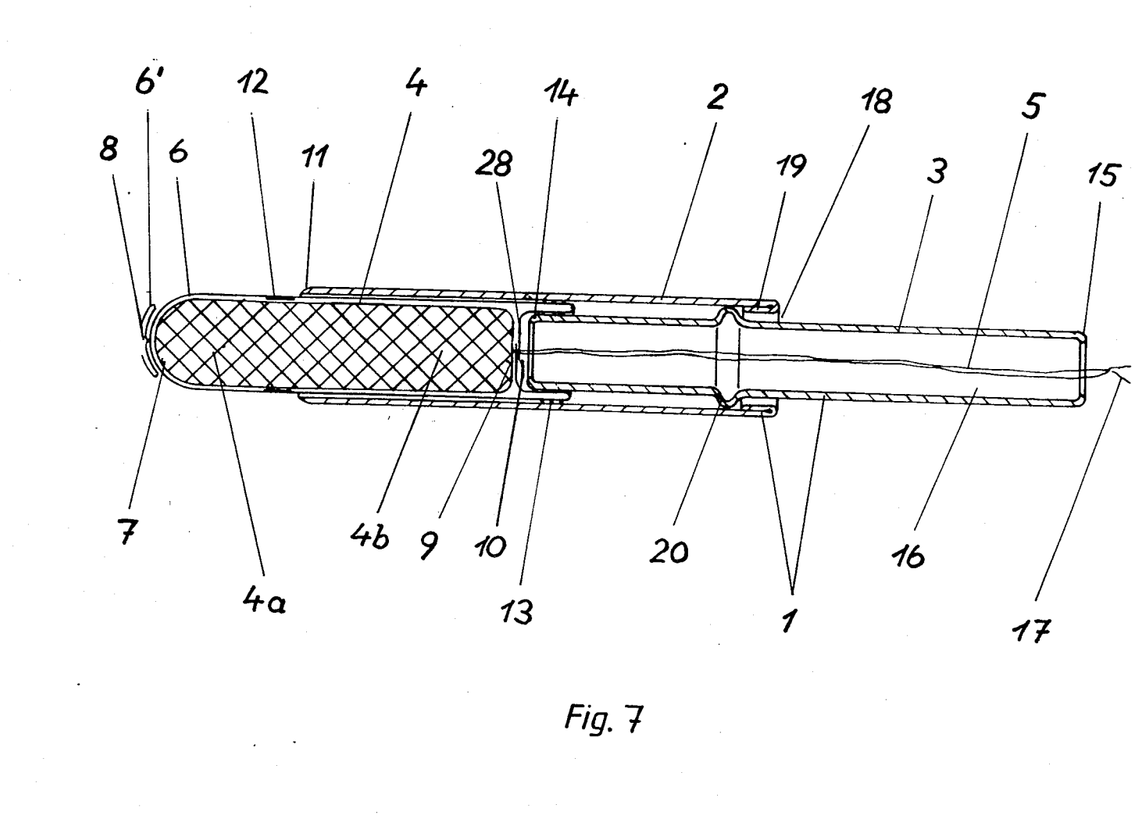

According to FIG. 7, the packaging film 6 has, at the rear end 9 of the tampon 4, a tamp-in portion 28 which is coaxial to the applicator shell 2 and into which the front end 14 of the plunger 3 engages. This has the advantage that, in the zone of the tamp-in portion 28, the packaging film 6 can easily be sealed from the inside to the applicator shell 2 by means of an expandable sealing mandrel not shown in the drawing. In this way, a faster heat transfer to the packaging film 6 during sealing is obtained than in the case of supplying heat via the outside of the applicator shell 2.

Figures 8, 9:
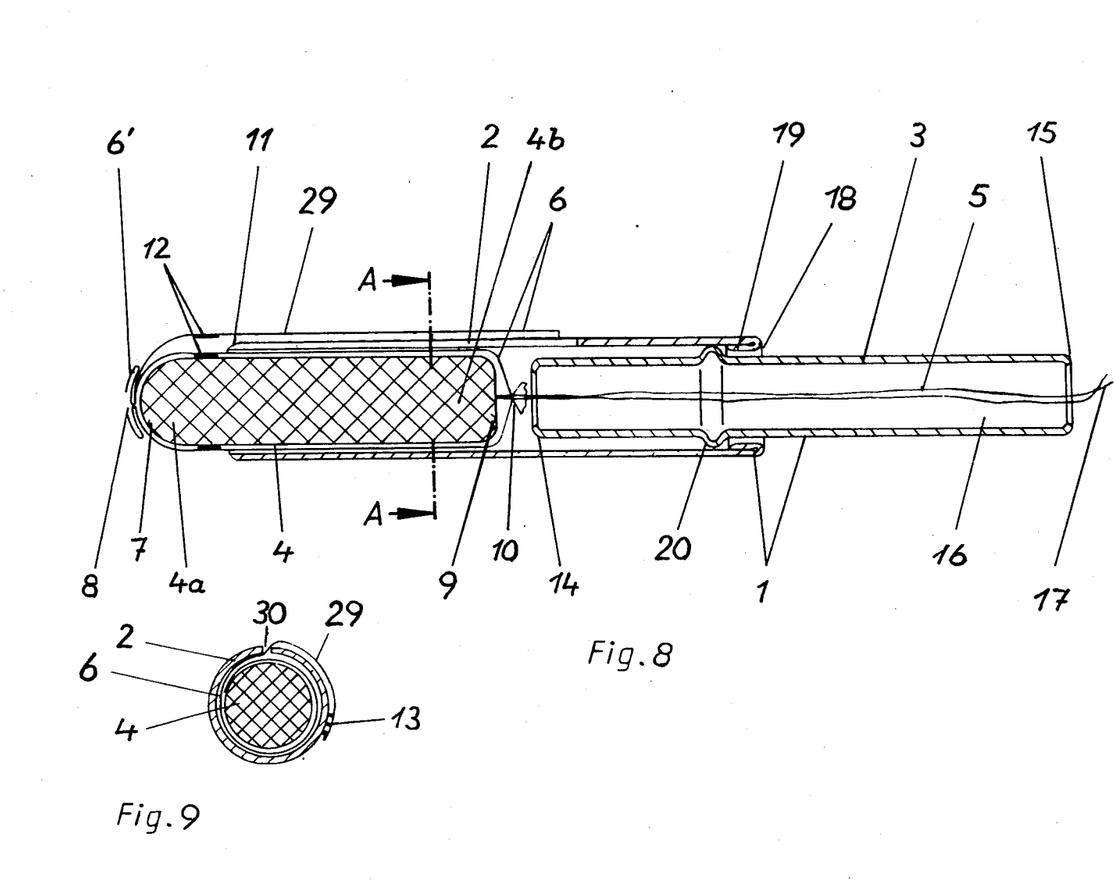

According to FIG. 8, the packaging film 6 is provided, on the outside of the applicator shell 2, with a fixing strap 29 which forms a constituent of the packaging film 6 and is led out from the applicator shell 2 through an axial slot 30 in the latter. The slot 30 extends up to the introduction end 11 of the applicator shell 2. On the outside of the applicator shell 2, the fixing strap 29 is fixed to junctions 13, for example by means of gluing or sealing.

In FIG. 9, a cross-section through the tampon pack according to FIG. 8, along the section line A—A is represented and this shows that the packaging film 6 surrounds the tampon 4 and overlaps itself over a short section in the region of the axial slot 30 of the applicator shell 2.

The tampon packs described above are suitable for all usual hygienic tampons.

The applicator shell 2 and the plunger 3 can consist of conventional materials, for example of plastic or little cardboard tubes.

I claim:

1. In a tampon pack, in particular for female hygiene comprising:
    a tampon having an introduction end and a rear end; said tampon disposed in an applicator shell open at both the introduction end and the rear end; a plunger telescopically mounted in said rear end of said applicator shell and axially moveable therein to push said tampon out of said applicator shell; the improvement comprising:
    said tampon being essentially totally enclosed, within said applicator shell, by a flexible packaging film; said film being formed into a closure adjacent the rear end of said tampon; said film being affixed to said applicator shell; opening means in said film for opening the film to allow the passage of the introduction end of the tampon therethrough;
    whereby, said tampon is protected from humidity prior to use and may be ejected from said shell by operating said opening means and pushing said tampon from said shell with said plunger while said film remains affixed to said shell.

2. The tampon pack of claim 1 wherein said opening means comprise a tear strip at the introduction end of the film.

3. The tampon pack of claim 1 wherein said opening means comprise a closure at the introduction end of said film, said closure being openable by the pressure exerted there against as the plunger ejects said tampon.

4. The tampon pack of claim 1 wherein said film is affixed to the inside surface of said shell.

5. The tampon pack of claim 4 wherein said film extends beyond said closure at the rear end of said tampon and said extended portion is affixed to the inside surface of said shell.

6. The tampon pack of claim 1 wherein said film is affixed to the outside surface of said shell.

7. The tampon pack of claim 6 wherein said film extends beyond said introduction end of said tampon and is folded back and affixed to the outer surface of said application shell.

* * * * *